(12) United States Patent
Gasem et al.

(10) Patent No.: US 6,392,115 B1
(45) Date of Patent: May 21, 2002

(54) SEPARATION OF HYDROCARBONS BY EXTRACTIVE DISTILLATION

(75) Inventors: Khaled A. M. Gasem; Robert L. Robinson, Jr., both of Stillwater, OK (US); Christopher J. Schult, Columbia, MD (US); Barbara A. Todd, Niotaze, KS (US)

(73) Assignee: Phillips Petroleum Company, Bartlesville, OK (US)

( * ) Notice: Subject to any disclaimer, the term of this patent is extended or adjusted under 35 U.S.C. 154(b) by 0 days.

(21) Appl. No.: 09/664,904

(22) Filed: Sep. 18, 2000

(51) Int. Cl.[7] .............................. C07C 7/00; C07C 7/10
(52) U.S. Cl. ...................... 585/808; 833/860; 833/865; 833/807
(58) Field of Search ................... 585/808, 833, 585/860, 865, 807

(56) References Cited

U.S. PATENT DOCUMENTS

| | | | |
|---|---|---|---|
| 5,135,617 A | 8/1992 | Brown et al. ................. | 203/56 |
| 5,200,174 A | 4/1993 | Gardlik et al. ................ | 424/66 |
| 5,491,037 A | 2/1996 | Kawakami .................... | 429/49 |
| 5,882,389 A | 3/1999 | Schwartz, Jr. ........... | 106/31.49 |

Primary Examiner—Walter D. Griffin
Assistant Examiner—Tam M. Nguyen
(74) Attorney, Agent, or Firm—Jeffrey R. Anderson

(57) ABSTRACT

A process for separating a first hydrocarbon, selected from the group consisting of aromatic hydrocarbons, cycloalkanes, cycloalkenes, cycloalkadienes and combinations thereof, from a close-boiling second hydrocarbon, selected from the group consisting of alkanes, alkenes, and alkadienes and combinations thereof, by extractive distillation of a hydrocarbon-containing fluid containing such hydrocarbons by using a solvent containing a 3-alkyl-substituted-2-oxazolidinone. Such aromatic hydrocarbons contain in the range of from about 6 to about 10 carbon atoms per molecule. Such cycloalkanes, cycloalkenes, cycloalkadienes, and close-boiling second hydrocarbon contain in the range of from about 4 to about 10 carbon atoms per molecule.

36 Claims, 1 Drawing Sheet

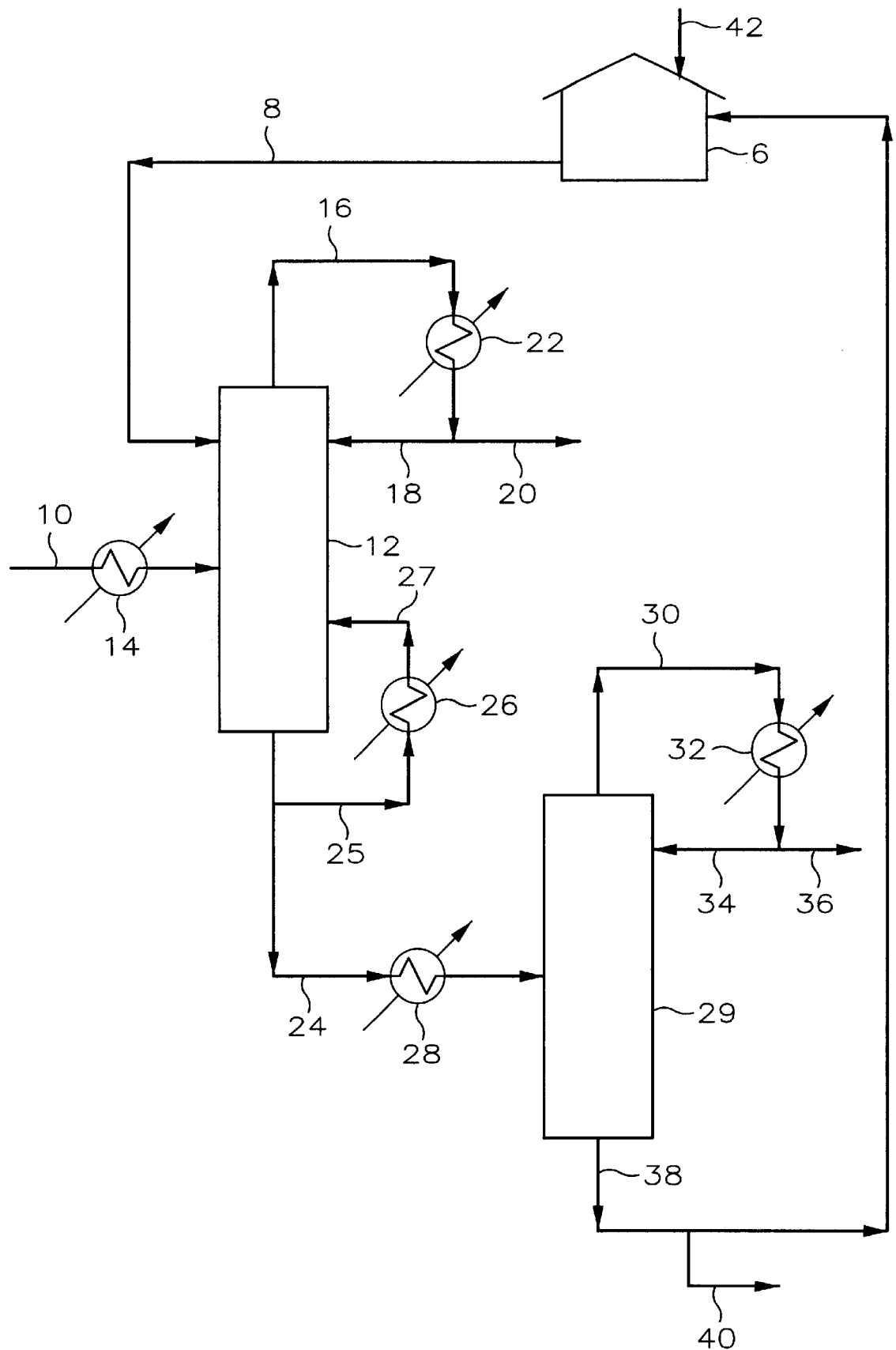

SEPARATION OF HYDROCARBONS BY EXTRACTIVE DISTILLATION

BACKGROUND OF THE INVENTION

This invention relates to the separation of at least one first hydrocarbon from at least one close-boiling second hydrocarbon by extractive distillation.

Extractive distillation is a well known technique for separating mixtures of components having a relative volatility close to unity (i.e., having nearly equal volatility and having nearly the same boiling point). It is difficult to separate the components of such mixtures by conventional fractional distillation. In extractive distillation, a solvent is introduced into a distillation column above the entry point of the hydrocarbon-containing fluid mixture which is to be separated. The solvent affects the volatility of the hydrocarbon-containing fluid component(s) boiling at higher temperatures (i.e., high-boiling components) differently than the hydrocarbon-containing fluid component(s) boiling at lower temperatures (i.e., low-boiling components) sufficiently to facilitate the separation of the various hydrocarbon-containing fluid components by distillation and such solvent exits with the bottoms fraction, as has been described in the article entitled Extractive Distillation Saves Energy by Ian Sucksmith, Chemical Engineering, Jun. 28, 1982, pages 91–95. Additional information on extractive distillation techniques can be found in Perry's Chemical Engineers' Handbook, Sixth Edition, McGraw-Hill, Inc., copyright 1984, pages 13–53 to 13–57.

SUMMARY OF THE INVENTION

It is an object of this invention to provide a process for separating at least one first hydrocarbon from at least one close-boiling second hydrocarbon different from said at least one first hydrocarbon by extractive distillation using a selective solvent (also referred to as extractant or entrainer). Other objects and advantages will be apparent from the detailed description of the invention and the appended claims.

In accordance with this invention, a process for separating at least one first hydrocarbon, selected from the group consisting of aromatic hydrocarbons, cycloalkanes, cycloalkenes, cycloalkadienes, and the like and combinations thereof, from at least one close-boiling second hydrocarbon selected from the group consisting of alkanes, alkenes, alkadienes, and the like and combinations thereof by extractive distillation of a hydrocarbon-containing fluid comprising said at least one first hydrocarbon and at least one close-boiling second hydrocarbon by using a solvent comprising a 3-alkyl-substituted-2-oxazolidinone.

BRIEF DESCRIPTION OF THE DRAWING

The FIGURE illustrates an extractive distillation process of the present invention.

DETAILED DESCRIPTION OF THE INVENTION

In an extractive distillation process, an agent (called "solvent" or "extractant" or "entrainer") is added to a hydrocarbon-containing fluid comprising components to be separated so that the relative volatilities of the components of the hydrocarbon-containing fluid are changed such that a sufficient difference in volatility of the components is established and effective separation by distillation becomes possible. The added solvent is usually chosen so as to exhibit high "selectivity" regarding the components to be separated. Selectivity is a term related to the relative volatilities of components in the hydrocarbon-containing fluid in the presence of the solvent. The larger the difference in the relative volatilities of the components in the hydrocarbon-containing fluid, the easier the separation of the components by fractional distillation. Therefore, a solvent of high selectivity is a solvent which causes great differences between the relative volatilities of the components in a hydrocarbon-containing fluid and will allow for the separation of components in a hydrocarbon-containing fluid with fewer distillation stages, lower amount of reflux, and higher product purity.

The term "close-boiling second hydrocarbon" as used herein, means that the at least one second hydrocarbon(s) selected from the group consisting of alkanes, alkenes, alkadienes, and the like and combinations thereof contained in the hydrocarbon-containing fluid has nearly the same boiling point as the at least one first hydrocarbon(s) selected from the group consisting of aromatic hydrocarbons containing in the range of from about 6 to about 10 carbon atoms per molecule, cycloalkanes, cycloalkenes, cycloalkadienes, and the like and combinations thereof contained in such hydrocarbon-containing fluid at atmospheric pressure or other pressure(s) of interest. The term "fluid" denotes gas, liquid, vapor, and combinations thereof.

In a process of this invention, any hydrocarbon-containing fluid which comprises at least one first hydrocarbon, selected from the group consisting of aromatic hydrocarbons, cycloalkanes, cycloalkenes, cycloalkadienes, and the like and combinations thereof, and at least one close-boiling second hydrocarbon(s), selected from the group consisting of alkanes, alkenes, alkadienes, and the like and combinations thereof, can be used in an extractive distillation process of the present invention. The aromatic hydrocarbons generally contain in the range of from about 6 to about 10 carbon atoms per molecule. The cycloalkanes, cycloalkenes, cycloalkadienes, alkanes, alkenes, and alkadienes generally contain in the range of from about 4 to about 10 carbon atoms per molecule.

The boiling points (at atmospheric pressure conditions, i.e., at about 1 atmosphere) of the at least one first hydrocarbon and of the at least one close-boiling second hydrocarbon to be separated by an extractive distillation process of the present invention are generally in the range of from about 100° F. to about to 500° F., preferably in the range of from about 100° F. to about 450° F. and, more preferably, in the range of from 100° F. to 400° F.

Generally, the hydrocarbon-containing fluid comprises at least one first hydrocarbon, selected from the group consisting of aromatic hydrocarbons, cycloalkanes, cycloalkenes, cycloalkadienes, and the like and combinations thereof, in any suitable amount which provides a hydrocarbon-containing fluid suitable for use in a process(es) of the present invention. Generally, the hydrocarbon-containing fluid comprises at least one first hydrocarbon in an amount up to about 99.9 weight percent first hydrocarbon based on the total weight of the hydrocarbon-containing fluid, preferably in the range of from about 0.1 to about 99.9 weight percent first hydrocarbon based on the total weight of the hydrocarbon-containing fluid, more preferably in the range of from about 0.5 to about 99.5 weight percent first hydrocarbon and, even more preferably, in the range of from 1 to 99 weight percent first hydrocarbon. When more than one type of at least one first hydrocarbon, selected from the group consisting of aromatic hydrocarbons, cycloalkanes, cycloalkenes, cycloalkadienes, and the like and combinations thereof, are present in the hydrocarbon-containing fluid, such first hydrocarbons can be present in any combination and any weight ratio. Suitable examples of mixtures of first hydrocarbons include, but are not limited to: aromatic hydrocarbon(s) and cycloalkane(s); aromatic hydrocarbon(s) and cycloalkene(s); aromatic hydrocarbon(s) and cycloalkadiene(s); aromatic hydrocarbon(s), cycloalkane(s), and cycloalkene(s); aromatic hydrocarbon(s), cycloalkene(s), and cycloalkadiene(s); aromatic hydrocarbon(s), cycloalkane(s), and cycloalkadiene(s); aromatic hydrocarbon(s), cycloalkane(s), cycloalkene(s) and cycloalkadiene(s); cycloalkane(s) and cycloalkene(s); cycloalkane(s) and cycloalkadiene(s); cycloalkene(s) and cycloalkadiene(s); and cycloalkane(s), cycloalkene(s) and cycloalkadiene(s); and the like and combinations thereof.

Generally, the hydrocarbon-containing fluid comprises at least one close-boiling second hydrocarbon, selected from the group consisting of alkanes, alkenes, alkadienes, and the like and combinations thereof, in any suitable amount which provides a hydrocarbon-containing fluid suitable for use in a process(es) of the present invention. Generally, the hydrocarbon-containing fluid comprises at least one close-boiling second hydrocarbon in an amount up to about 99.9 weight percent close-boiling second hydrocarbon based on the total weight of the hydrocarbon-containing fluid, preferably, the hydrocarbon-containing fluid comprises at least one close-boiling second hydrocarbon in an amount in the range of from about 0.1 to about 99.9 weight percent close-boiling second hydrocarbon based on the total weight of the hydrocarbon-containing fluid, more preferably in the range of from about 0.5 to about 99.5 weight percent close-boiling second hydrocarbon and, even more preferably, in the range of from 1 to 99 weight percent close-boiling second hydrocarbon. When more than one type of at least one close-boiling second hydrocarbon, selected from the group consisting of alkanes, alkenes, alkadienes, and the like and combinations thereof, are present in the hydrocarbon-containing fluid, such close-boiling second hydrocarbons can be present in any combination and any weight ratio. Suitable examples of mixtures of close-boiling second hydrocarbons include, but are not limited to: alkane(s) and alkene(s); alkane(s) and alkadiene(s); alkene(s) and alkadiene(s); and alkane(s), alkene(s) and alkadiene(s); and the like and combinations thereof.

Examples of suitable alkanes include, but are not limited to, butane, pentane, methylbutanes (such as 2-methylbutane), hexane, dimethylbutanes (such as 2,2-dimethylbutane and 2,3-dimethylbutane), methylpentanes (such as 2-methylpentane and 3-methylpentane), heptane, trimethylbutanes (such as 2,2,3-trimethylbutane), dimethylpentanes (such as 2,2-dimethylpentane, 2,4-dimethylpentane, and 3,3-dimethylpentane), methylhexanes (such as 2-methylhexane and 3-methylhexane), octane, trimethylpentanes (such as 2,2,4-trimethylpentane), dimethylhexanes (such as 2,4-dimethylhexane), methylheptanes (such as 2-methylheptane), nonane, dimethylheptanes (such as 2,3-dimethylheptane), decane, and the like and combinations thereof.

Preferred alkanes include, but are not limited to, pentane, methylbutanes, hexane, dimethylbutanes, heptane, trimethylbutanes, dimethylpentanes, and the like and combinations thereof. More preferred alkanes include pentane, 2-methylbutane, hexane, 2,2-dimethylbutane, heptane, 2,2,3-trimethylbutane, 2,2-dimethylpentane, and 2,4-dimethylpentane.

Examples of suitable alkenes (i.e., aliphatic monoolefins) include, but are not limited to, pentenes (such as 1-pentene and 2-pentene), methyl-1-butenes (such as 2-methyl-1-butene), methyl-2-butenes (such as 2-methyl-2-butene), hexenes (such as 1-hexene, 2-hexene, and 3-hexene), dimethylbutenes (such as 2,3-dimethyl-1-butene), methylpentenes (such as 2-methyl-1-pentene, 2-methyl-2-pentene, and 3-methyl-1-pentene), heptenes (such as 1-heptene, 2-heptene, and 3-heptene), methylhexenes (such as 2-methyl-1-hexene), octenes (such as 1-octene, 2-octene, and 3-octene), methylheptenes (such as 2-methyl-1-heptene), nonenes (such as 1-nonene, 2-nonene, 3-nonene), decenes (such as 1-decene), and the like and combinations thereof.

Preferred alkenes include, but are not limited to, pentenes, methyl-1-butenes, methyl-2-butenes, hexenes, dimethylbutenes, methylpentenes, heptenes, and the like and combinations thereof. More preferred alkenes include 1-pentene, 2-pentene, 2-methyl-1-butene, 2-methyl-2-butene, 1-hexene, 2-hexene, 3-hexene, 2,3-dimethyl-1-butene, 2-methyl-1-pentene, 2-methyl-2-pentene, 3-methyl-1-pentene, 1-heptene, 2-heptene, and 3-heptene.

Examples of suitable alkadienes (i.e., aliphatic diolefins) include, but are not limited to, butadienes (such as 1,2-butadiene and 1,3-butadiene), pentadienes (such as isoprene, 1,3-pentadiene, and 1,4-pentadiene), hexadienes (such as 1,3-hexadiene, 1,4-hexadiene, 1,5-hexadiene, and 2,4-hexadiene), dimethylbutadienes (such as 2,3-dimethyl-1,3-butadiene), methylpentadienes (such as 2-methyl-1,3-pentadiene), heptadienes (such as 1,6-heptadiene), methylhexadienes (such as 2-methyl-1,5-hexadiene), octadienes (such as 1,7-octadiene), nonadienes (such as 1,8-nonadiene), methyloctadienes (such as 7-methyl-1,6-octadiene), and the like and combinations thereof.

Preferred alkadienes include, but are not limited to, pentadienes, hexadienes, dimethylbutadienes, heptadienes, and the like and combinations thereof. More preferred alkadienes include isoprene, 1,3-pentadiene, 1,4-pentadiene, 1,3-hexadiene, 1,4-hexadiene, 1,5-hexadiene, 2,4-hexadiene, 2,3-dimethyl-1,3-butadiene, and 1,6-heptadiene.

Examples of suitable aromatic hydrocarbons include, but are not limited to, benzene, toluene, meta-xylene, ortho-xylene, para-xylene, ethylbenzene, trimethylbenzenes, methylethylbenzenes, and the like and combinations thereof. Preferred aromatic hydrocarbons include, but are not limited to, benzene, toluene, meta-xylene, ortho-xylene, para-xylene, and the like and combinations thereof. More preferred aromatic hydrocarbons include benzene and toluene.

Examples of suitable cycloalkanes include, but are not limited to, cyclopentane, cyclohexane, methylcyclopentane, cycloheptane, ethylcyclopentane, methylcyclohexane, cyclooctane, dimethylcyclohexanes (such as 1,2-dimethylcyclohexane and 1,3-dimethylcyclohexane), ethylcyclohexane, cyclononane, cyclodecane, and the like and combinations thereof.

Preferred cycloalkanes include, but are not limited to, cyclopentane, cyclohexane, cycloheptane, and the like and combinations thereof. More preferred cycloalkanes include cyclopentane and cyclohexane.

Examples of suitable cycloalkenes include, but are not limited to, cyclopentene, cyclohexene, methylcyclopentenes (such as 1-methyl-1-cyclopentene), cycloheptene, methylcyclohexenes (such as 1-methyl-1-cyclohexene and 4-methyl-1-cyclohexene), cyclooctene, and the like and combinations thereof.

Preferred cycloalkenes include, but are not limited to, cyclopentene, cyclohexene, cycloheptene, and the like and combinations thereof. More preferred cycloalkenes include cyclopentene and cyclohexene.

Examples of suitable cycloalkadienes include, but are not limited to, cyclohexadienes (such as 1,3-cyclohexadiene), cycloheptadienes (such as 1,3-cycloheptadiene), methylcyclohexadienes (such as 1-methyl-1,4-cyclohexadiene), cyclooctadienes (such as 1,5-cyclooctadiene), and the like and combinations thereof.

Preferred cycloalkadienes include, but are not limited to, cyclohexadienes, cycloheptadienes, and the like and combinations thereof. More preferred cycloalkadienes include 1,3-cyclohexadiene and 1,3-cycloheptadiene.

A preferred hydrocarbon-containing fluid comprises at least one first hydrocarbon selected from the group consisting of benzene, toluene, meta-xylene, ortho-xylene, para-xylene, and the like and combinations thereof, and at least one close-boiling second hydrocarbon selected from the group consisting of pentane, 2-methylbutane, hexane, 2,2-dimethylbutane, heptane, 2,2,3-trimethylbutane, 2,2-dimethylpentane, 2,4-dimethylpentane, and the like and combinations thereof. Another preferred hydrocarbon-containing fluid comprises at least one first hydrocarbon selected from the group consisting of cyclopentane, cyclohexane, cycloheptane, 1,2-dimethylcyclopentane, 2,3-dimethylcyclopentane, and the like and combinations thereof, and at least one close-boiling second hydrocarbon selected from the group consisting of pentane, 2-methylbutane, hexane, 2,2-dimethylbutane, heptane, 2,2,3-trimethylbutane, 2,2-dimethylpentane, 2,4-dimethylpentane, and the like and combinations thereof.

A more preferred hydrocarbon-containing fluid comprises at least one first hydrocarbon, selected from the group consisting of benzene, toluene, and combinations thereof, and at least one close-boiling second hydrocarbon selected from the group consisting of pentane, 2-methylbutane, hexane, 2,2-dimethylbutane, heptane, 2,2,3-trimethylbutane, 2,2-dimethylpentane, 2,4-dimethylpentane, and combinations thereof. Another more preferred hydrocarbon-containing fluid comprises at least one first hydrocarbon, selected from the group consisting of cyclopentane, cyclohexane, and combinations thereof, and at least one close-boiling second hydrocarbon selected from the group consisting of pentane, 2-methylbutane, hexane, 2,2-dimethylbutane, heptane, 2,2,3-trimethylbutane, 2,2-dimethylpentane, 2,4-dimethylpentane and combinations thereof.

The solvent of the present invention comprises a 3-alkyl-substituted-2-oxazolidinone having the formula:

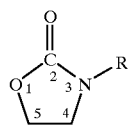

wherein the functional group R at the 3 position is an alkyl selected from the group consisting of methyl, ethyl, propyl, and butyl (i.e., the functional group R at the 3 position is a $C_1$–$C_4$ alkyl). Preferably, the functional group R at the 3 position is an alkyl selected from the group consisting of methyl and ethyl (i.e., the functional group R at the 3 position is a $C_1$–$C_2$ alkyl). More preferably, the functional group R at the 3 position is methyl (i.e., the functional group R at the 3 position is a $C_1$ alkyl).

Generally, the solvent comprises a 3-alkyl-substituted-2-oxazolidinone selected from the group consisting of 3-methyl-2-oxazolidinone, 3-ethyl-2-oxazolidinone, 3-propyl-2-oxazolidinone, 3-butyl-2-oxazolidinone, and the like and combinations thereof. Preferably, the solvent comprises a 3-alkyl-substituted-2-oxazolidinone selected from the group consisting of 3-methyl-2-oxazolidinone, 3-ethyl-2-oxazolidinone, and the like and combinations thereof. The more preferred 3-alkyl-substituted-2-oxazolidinone is 3-methyl-2-oxazolidinone (i.e., the more preferred solvent is 3-methyl-2-oxazolidinone).

The 3-alkyl-substituted-2-oxazolidinone may also have substituents located at the 4 and 5 positions of the heterocyclic ring instead of hydrogen. Generally, if used, such substituents are lower alkyls, e.g., $C_1$–$C_4$ alkyl, preferably $C_1$–$C_2$ alkyl, and more preferably a $C_1$ alkyl (i.e., methyl).

The 3-alkyl-substituted-2-oxazolidinone can be made by any manner or method(s) known in the art (an example process is disclosed in U.S. Pat. No. 2,755,286). 3-Methyl-2-oxazolidinone is commercially available, for example, from Aldrich Chemical Company (Milwaukee, Wis., United States of America).

Any suitable weight ratio of the solvent, comprising a 3-alkyl-substituted-2-oxazolidinone, to the hydrocarbon-containing fluid can be used. Generally, the solvent to hydrocarbon-containing fluid weight ratio is in the range of from about 1:1 to about 40:1, preferably in the range of from about 2:1 to about 25:1 and, more preferably, in the range of from 3:1 to 20:1.

Any suitable reflux ratio (i.e., the weight ratio of the portion of condensed vapor which is returned to the distillation column to the portion of condensed vapor which is withdrawn as distillate product) can be used in an extractive distillation process of the present invention. The reflux ratio is generally in the range of from about 0.1:1 to about 100:1, preferably in the range of from about 0.5:1 to about 50:1 and, more preferably, in the range of from 1:1 to 20:1.

Any suitable hydrocarbon-containing fluid entry location can be selected. Generally the hydrocarbon-containing fluid entry location is in the range of from about 2 percent of the total height of the packed or trayed column, measured upward from the bottom of the column, to about 70 percent, preferably in the range of from about 5 percent to about 60 percent and, more preferably, in the range of from 7 percent to 70 percent.

Any suitable solvent entry location can be selected. Generally the solvent entry location is in the range of from about 50 percent of the total height of the packed or trayed column (i.e., within the upper half of the column) to about 99 percent, preferably in the range of from about 70 percent to about 99 percent and, more preferably, in the range of from 80 percent to 99 percent.

Any suitable temperature in the reboiler vessel (containing primarily the high-boiling hydrocarbon-containing fluid components and the solvent) can be used. The temperature is generally in the range of from about 200° F. to about 500° F., preferably in the range of from about 250° F. to about 450° F. and, more preferably, in the range of from 300° F. to 400° F.

The extractive distillation column is generally heated more near the bottom and less near the top. Generally, the temperature at the top of the column where the vapor exits into the condenser is in the range of from about 80° F. to about 350° F., preferably in the range of from about 100° F. to about 250° F. and, more preferably, in the range of from 125° F. to 225° F. The solvent and hydrocarbon-containing fluid are generally preheated (generally to a temperature close to the column temperature of the corresponding entry point) before they are introduced into the column. Any suitable pressure can be used during the extractive distillation. Generally the pressure is in the range of from about 5 pounds per square inch gauge (psig) to about 100 psig, preferably in the range of from about 8 psig to about 25 psig and, more preferably, in the range of from 10 psig to 20 psig.

The overhead distillate product (withdrawn from the top of the column) generally comprises a smaller volume percentage of the first hydrocarbon(s) (i.e., high-boiling components) such as aromatic hydrocarbon(s), cycloalkane(s), cycloalkene(s), and cycloalkadiene(s) than the hydrocarbon-containing fluid introduced into the column and a larger volume percentage of the close-boiling second hydrocarbon(s) (i.e., low-boiling components) such as alkane(s), alkene(s), and alkadiene(s) than the hydrocarbon-containing fluid introduced into the column. The bottoms product (a portion of which can be reheated and recycled to the lower portion of the column) generally comprises a larger volume percentage of the first hydrocarbon(s) (i.e., high-boiling components) such as aromatic hydrocarbon(s), cycloalkane(s), cycloalkene(s), and cycloalkadiene(s) than the hydrocarbon-containing fluid introduced into the column and a smaller volume percentage of the close-boiling second hydrocarbon(s) (i.e., low-boiling components) such as alkane(s), alkene(s), and alkadiene(s) than the hydrocarbon-containing fluid introduced into the column. Furthermore, the bottoms product comprises essentially all of the added solvent which can be separated from the other bottoms product components by distillation or other suitable separating means and then recycled to the extractive distillation column.

Any suitable total column height, packed column height, column diameter and number of trays in the extraction distillation column can be used. The dimensions and column designs depend on the scale of the operation, the hydrocarbon-containing fluid composition, the solvent composition, the desired recovery and degree of purity of the various product, and the like, and can be determined by those having ordinary skill in the art.

The invention can be better understood by reference to the FIGURE and the following description of a preferred embodiment of the invention. The hydrocarbon-containing fluid comprising at least one first hydrocarbon and at least one close-boiling second hydrocarbon is introduced through conduit 10 to a fractionation zone such as multi-stage distillation column 12. The temperature of the hydrocarbon-containing fluid flowing through conduit 10 can be adjusted as needed by controlling heat exchanger 14 so as to add heat to, or remove heat from, the hydrocarbon-containing fluid. Solvent from solvent storage 6 is introduced to distillation column 12 through conduit 8, and an overhead stream is withdrawn from an upper portion of distillation column 12 through conduit 16. This overhead stream can be completely passed to storage or to other processing units or, as is often the case, the overhead stream can be partially or totally condensed, with a portion thereof being returned to the fractionation zone as reflux. The overhead stream passing through conduit 16 is condensed in condenser 22 to yield a condensed overhead stream. A portion of the condensed overhead stream can be returned to distillation column 12 as reflux through conduit 18, while the remainder of the condensed overhead stream is yielded as product or passed to other processing units through conduit 20.

A bottoms stream is withdrawn from a lower portion of the fractionation zone represented by distillation column 12 through conduit 24. A portion of the fluids withdrawn from the bottom of distillation column 12 may be heated and returned to distillation column 12. For example, a portion of the bottoms product stream can be withdrawn through conduit 25, heated in reboiler 26 and then passed back to a lower portion of distillation column 12 through conduit 27.

Operating conditions in heat exchanger 14, condenser 22 and reboiler 26 can be controlled and interfaced with solvent flow through conduit 8, hydrocarbon-containing fluid flow through conduit 10, reflux flow through conduit 18 and bottoms stream flow through conduit 24 such that the hydrocarbon-containing fluid introduced into distillation column 12 will be fractionated to yield an overhead stream comprising the low-boiling component(s) such as alkane(s), alkene(s), and alkadiene(s) and a bottoms stream comprising the solvent and the high-boiling component(s) such as aromatic hydrocarbon(s), cycloalkane(s), cycloalkene(s), and cycloalkadiene(s).

The bottoms stream passing through conduit 24 can be passed to storage, used in other processes or, preferably, passed to another fractionation zone, such as distillation column 29. Any adjustments to the temperature of the bottoms stream passing through conduit 24 necessary for efficient fractionation in distillation column 29 can be made by appropriately adjusting heat exchanger 28. An overhead stream predominantly comprising the high-boiling component(s) such as aromatic hydrocarbon(s), cycloalkane(s), cycloalkene(s), and cycloalkadiene(s) is withdrawn from an upper portion of distillation column 29 through conduit 30. This overhead stream can be at least partially condensed in condenser 32. A portion of the overhead stream withdrawn from condenser 32 can be returned through conduit 34 as reflux for distillation column 29, with the remainder of the overhead stream being withdrawn as product, e.g., aromatic hydrocarbon(s) of high purity (preferably higher than 95%), through conduit 36.

A bottoms stream predominantly comprising the solvent is withdrawn from a lower portion of distillation column 29 through conduit 38. A portion of this bottoms stream is preferably routed back to solvent storage 6 and then recycled to distillation column 12, while another portion of the bottoms stream is heated in a reboiler (not shown) and returned to the lower portion of column 29. From time to time, impurities which may build up in the solvent can be removed from the system by removing a small purge stream through conduit 40. Solvent lost through the purge stream or through other processing losses may be made up by a makeup stream passing through conduit 42 and into solvent storage 6.

The following examples are presented to further illustrate this invention and are not to be construed as unduly limiting the scope of this invention.

EXAMPLE I

This example demonstrates the use of 3-methyl-2-oxazolidinone as a solvent in an extractive distillation of a hydrocarbon-containing fluid comprising at least one first hydrocarbon(s) and at least one close-boiling second hydrocarbon(s).

The physical properties of the 3-methyl-2-oxazolidinone, obtained from Sigma-Aldrich, St. Louis, Mo., under the designation CAS-19836-78-3, included a melting point of 15° C., a boiling point of 88° C. at 1 mm Hg, and a specific gravity of 1.17.

The example experiments were conducted using gas-liquid partition chromatography as disclosed in the article by A. T. James and A. J. P. Martin entitled "Gas-liquid Partition Chromatography: the Separation and Micro-estimation of Volatile Fatty Acids from Formic Acid to Dodecanoic Acid" at pages 679–690 of Volume 50 of the Journal of Biochemistry (1952).

Example experiments were conducted in the following manner. A chromatographic column containing an inert support material of CHROMOSORB 750 obtained from Alltech, Deerfield, Ill., under the designation Lot Number 988, was coated with 20 to 30 percent by weight 3-methyl-2-oxazolidinone solvent which acted as the stationary phase. Helium was used as the carrier through the column. To minimize solvent weight loss due to stripping by the helium stream, two pre-saturator columns were situated approximately 30 feet and 1 foot, respectively, upstream from the chromatographic column. A heating coil was located between the two pre-saturator columns. An air bath obtained from Varian, Palo Alto, Calif., under the designation Model 3700, was used to maintain the chromatographic column at constant temperature. Approximately 0.1 microliter ($\mu L$) of a hydrocarbon solute was injected, using a gas injection port obtained from Varian, Palo Alto, Calif., under the designation Model 3700, into the helium stream approximately six inches upstream of the chromatographic column, following a similar injection of a reference inert solute (nitrogen). A thermal conductivity detector obtained from Varian, Palo Alto, Calif., under the designation Model 3700, was located approximately six inches downstream of the chromatographic column. The hydrocarbon solute was passed through the thermal conductivity detector concurrently with helium which had been passed through a pre-saturator column separate from the other two pre-saturator columns. The thermal conductivity detector was used to obtain retention times of the solutes.

Determining the infinite-dilution activity coefficient of a given hydrocarbon solute was based on measurements of the retention times of the solute and the reference solute, the weight of the 3-methyl-2-oxazolidinone solvent coated on the chromatographic column, the air bath temperature, and the inlet and outlet pressures of the chromatographic column. Using such measurements, the infinite-dilution activity coefficient for each solute hydrocarbon was determined as $$\gamma_i^\infty = \frac{wRT}{jp_i^s M(t_r - t_a)V_g \phi_i^s}$$

Where:
w=Mass of the solvent coated on the column
M=Molecular weight of the solvent
R=Universal gas constant
T=Absolute temperature of the air bath
$p_i^s$=Saturated vapor pressure of the solute
$V_g$=Volumetric flow rate of the carrier gas
$t_r$=Retention time of the hydrocarbon solute
$t_a$=Retention time of the reference inert solute
$\phi_i^s$=Solute fugacity coefficient at the saturation pressure
j=Martin's correction factor, which is $$j = 1.5 \left[ \frac{(p_i/p_o)^2 - 1}{(p_i/p_o)^3 - 1} \right],$$

where:
$p_i$ and $p_o$ are the column inlet and outlet pressures, respectively.

Tables I and II present the infinite-dilution activity coefficients that were measured for each hydrocarbon solute in the 3-methyl-2-oxazolidinone solvent at 40° C. and 50° C., respectively. The selectivity of the 3-methyl-2-oxazolidinone solvent was then determined for each pair of closing-boiling hydrocarbons targeted for separation as:

$$S_{ij} = \gamma_i^\infty / \gamma_j^\infty$$

where $\gamma_i^\infty$ is the infinite-dilution activity coefficient of the first hydrocarbon solute (e.g., benzene) and $\gamma_j^\infty$ is the infinite-dilution activity coefficient of the second hydrocarbon solute (e.g., pentane). Tables III and IV present the experimental selectivities for the 3-methyl-2-oxazolidinone solvent with various combinations of hydrocarbon solutes of interest at 40° C. and 50° C., respectively.

TABLE I

Experimental Infinite-dilution Activity Coefficients for Various Solutes in 3-Methyl-2-oxazolidinone at 40° C.

| Solute | $\gamma^\infty_i$ |
| --- | --- |
| Pentane | 20.5 |
| Hexane | 28.1 |
| Heptane | 39.1 |
| 2-Methylbutane | 18.6 |
| 2,2-Dimethylbutane | 24.6 |
| 2,2,3-Trimethylbutane | 28.4 |
| 2,2-Dimethylpentane | 34.9 |
| 2,4-Dimethylpentane | 36.8 |
| Benzene | 1.63 |
| Toluene | 2.38 |
| Cyclopentane | 10.9 |
| Cyclohexane | 16.1 |

TABLE II

Experimental Infinite-dilution Activity Coefficients for Various Solutes in 3-Methyl-2-oxazolidinone at 50° C.

| Solute | $\gamma^\infty_i$ |
| --- | --- |
| Pentane | 17.7 |
| Hexane | 24.9 |
| Heptane | 34.3 |
| 2-Methylbutane | 17.2 |
| 2,2-Dimethylbutane | 21.0 |
| 2,2,3-Trimethylbutane | 24.7 |
| 2,2-Dimethylpentane | 30.3 |
| 2,4-Dimethylpentane | 31.5 |
| Benzene | 1.60 |
| Toluene | 2.31 |
| Cyclopentane | 10.2 |
| Cyclohexane | 14.4 |

TABLE III

Experimental Selectivities for Various Solutes in 3-methyl-2-oxazolidinone at 40° C.

| | Benzene | Toluene | Cyclo-pentane | Cyclohexane |
| --- | --- | --- | --- | --- |
| Pentane | 12.6 | 8.6 | 1.9 | 1.3 |
| Hexane | 17.3 | 11.8 | 2.6 | 1.7 |
| Heptane | 24.1 | 16.5 | 3.6 | 2.4 |
| 2-Methylbutane | 11.5 | 7.8 | 1.7 | 1.2 |
| 2,2-Dimethylbutane | 15.1 | 10.3 | 2.2 | 1.5 |
| 2,2,3-Trimethylbutane | 17.4 | 11.9 | 2.6 | 1.8 |
| 2,2-Dimethylpentane | 21.5 | 14.7 | 3.2 | 2.2 |
| 2,4-Dimethylpentane | 22.6 | 15.5 | 3.4 | 2.3 |

TABLE IV

Experimental Selectivities for Various Solutes in 3-methyl-2-oxazolidinone at 50° C.

| | Benzene | Toluene | Cyclopentane | Cyclohexane |
|---|---|---|---|---|
| Pentane | 12.5 | 8.6 | 1.9 | 1.3 |
| Hexane | 17.3 | 11.9 | 2.6 | 1.7 |
| Heptane | 24.1 | 16.5 | 3.6 | 2.4 |
| 2-Methylbutane | 11.7 | 8.0 | 1.7 | 1.2 |
| 2,2-Dimethylbutane | 15.0 | 10.2 | 2.2 | 1.5 |
| 2,2,3-Trimethylbutane | 17.1 | 11.7 | 2.6 | 1.7 |
| 2,2-Dimethylpentane | 21.2 | 14.5 | 3.2 | 2.1 |
| 2,4-Dimethylpentane | 19.0 | 13.0 | 2.9 | 1.9 |

Test data in Tables I–IV clearly demonstrate that 3-methyl-2-oxazolidinone is effective as a solvent in an extractive distillation of a hydrocarbon-containing fluid comprising at least one first hydrocarbon(s) and at least one close-boiling second hydrocarbon(s).

EXAMPLE II

This example demonstrates a comparison between 3-methyl-2-oxazolidinone (a nitrogen-based solvent) and sulfolane (a sulfur-based solvent) in an extractive distillation of a hydrocarbon-containing fluid comprising at least one first hydrocarbon(s) and at least one close-boiling second hydrocarbon(s).

The physical properties of the 3-methyl-2-oxazolidinone, obtained from Sigma-Aldrich, St. Louis, Mo., under the designation CAS Number 19836-78-3, included a melting point of 15° C., a boiling point of 88° C. at 1 mm Hg, and a specific gravity of 1.17.

The physical properties of the sulfolane, obtained from Phillips Petroleum Company, Bartlesville, Okla., under the designation CAS 126-783-1, included a melting point of 27° C., a boiling point of 285° C. at 760 mm Hg, and a specific gravity of 1.261.

Example runs were conducted in the same manner as Example I with the exception that sulfolane was used as the solvent instead of 3-methyl-2-oxazolidinone. Test results comparing 3-methyl-2-oxazolidinone with sulfolane are summarized in Table V.

TABLE V

Experimental Selectivities for Various Solutes in 3-methyl-2-oxazolidinone at 50° C. and for Various Solutes in sulfolane at 50° C.

| | Benzene | | Toluene | | Cyclopentane | | Cyclohexane | |
|---|---|---|---|---|---|---|---|---|
| | 3M2OX* | Sulfolane | 3M2OX | Sulfolane | 3M2OX | Sulfolane | 3M2OX | Sulfolane |
| Pentane | 12.5 | 11.6 | 8.6 | 7.4 | 1.9 | 1.8 | 1.3 | 1.2 |
| Hexane | 17.3 | 18.0 | 11.9 | 11.5 | 2.6 | 2.8 | 1.7 | 1.9 |
| Heptane | 24.1 | 25.0 | 16.5 | 16.0 | 3.6 | 3.9 | 2.4 | 2.7 |
| 2-Methylbutane | 11.7 | 10.6 | 8.0 | 6.8 | 1.7 | 1.7 | 1.2 | 1.1 |

*3M2OX denotes 3-methyl-2-oxazolidinone

Test data in Table V demonstrate that 3-methyl-2-oxazolidinone is as effective as sulfolane as a solvent in an extractive distillation of a hydrocarbon-containing fluid comprising at least one first hydrocarbon(s) and at least one close-boiling second hydrocarbon(s).

The results shown in the above examples clearly demonstrate that the present invention is well adapted to carry out the objects and attain the ends and advantages mentioned as well as those inherent therein.

Reasonable variations, modifications, and adaptations can be made within the scope of the disclosure and the appended claims without departing from the scope of this invention.

What is claimed is:

1. A process for separating a first hydrocarbon from a close-boiling second hydrocarbon wherein said process comprises extractive distillation of a hydrocarbon-containing fluid comprising said first hydrocarbon and said close-boiling second hydrocarbon using a solvent comprising a 3-alkyl-substituted-2-oxazolidinone.

2. A process according to claim 1 wherein said first hydrocarbon is selected from the group consisting of aromatic hydrocarbons, cycloalkanes, cycloalkenes, cycloalkadienes, and combinations thereof and further wherein said aromatic hydrocarbons contain in the range of from about 6 to about 10 carbon atoms per molecule.

3. A process according to claim 2 wherein said close-boiling second hydrocarbon is selected from the group consisting of alkanes, alkenes, alkadienes, and combinations thereof.

4. A process according to claim 3 wherein said cycloalkanes, cycloalkenes, cycloalkadienes, alkanes, alkenes, and alkadienes contain in the range of from about 4 to about 10 carbon atoms per molecule.

5. A process according to claim 1 wherein the boiling points of said first hydrocarbon and said close-boiling second hydrocarbon are in the range of from about 100° F. to about 500° F.

6. A process according to claim 5 wherein the boiling points of said first hydrocarbon and said close-boiling second hydrocarbon are in the range of from about 100° F. to about 450° F.

7. A process according to claim 1 wherein said hydrocarbon-containing fluid comprises said first hydrocarbon in the range of from about 0.1 to about 99.9 weight percent first hydrocarbon based on the total weight of said hydrocarbon-containing fluid.

8. A process according to claim 1 wherein said hydrocarbon-containing fluid comprises said close-boiling second hydrocarbon in the range of from about 0.1 to about 99.9 weight percent close-boiling second hydrocarbon based on the total weight of said hydrocarbon-containing fluid.

9. A process according to claim 2 wherein said aromatic hydrocarbons are selected from the group consisting of benzene, toluene, meta-xylene, ortho-xylene, para-xylene, ethylbenzene, trimethylbenzenes, methylethylbenzenes, and combinations thereof.

10. A process according to claim 9 wherein said aromatic hydrocarbons are selected from the group consisting of benzene, toluene, meta-xylene, ortho-xylene, para-xylene, and combinations thereof.

11. A process according to claim 2 wherein said cycloalkanes are selected from the group consisting of cyclopentane, cyclohexane, methylcyclopentane, cycloheptane, ethylcyclopentane, methylcyclohexane, cyclooctane, dimethylcyclohexanes, ethylcyclohexane, cyclononane, cyclodecane, and combinations thereof.

12. A process according to claim 11 wherein said cycloalkanes are selected from the group consisting of cyclopentane, cyclohexane, cycloheptane, and combinations thereof.

13. A process according to claim 2 wherein said cycloalkenes are selected from the group consisting of cyclopentene, cyclohexene, methylcyclopentenes, cycloheptene, methylcyclohexenes, cyclooctene, and combinations thereof.

14. A process according to claim 13 wherein said cycloalkenes are selected from the group consisting of cyclopentene, cyclohexene, cycloheptene, and combinations thereof.

15. A process according to claim 2 wherein said cycloalkadienes are selected from the group consisting of cyclohexadienes, cycloheptadienes, methylcyclohexadienes, cyclooctadienes, and combinations thereof.

16. A process according to claim 15 wherein said cycloalkadienes are selected from the group consisting of cyclohexadienes, cycloheptadienes, and combinations thereof.

17. A process according to claim 3 wherein said alkanes are selected from the group consisting of butane, pentane, methylbutanes, hexane, dimethylbutanes, methylpentanes, heptane, trimethylbutanes, dimethylpentanes, methylhexanes, octane, trimethylpentanes, dimethylhexanes, methylheptanes, nonane, dimethylheptanes, decane, and combinations thereof.

18. A process according to claim 17 wherein said alkanes are selected from the group consisting of pentane, methylbutanes, hexane, dimethylbutanes, heptane, trimethylbutanes, dimethylpentanes, and combinations thereof.

19. A process according to claim 3 wherein said alkenes are selected from the group consisting of pentenes, methyl-1-butenes, methyl-2-butenes, hexenes, dimethylbutenes, methylpentenes, heptenes, methylhexenes, octenes, methylheptenes, nonenes, decenes, and combinations thereof.

20. A process according to claim 19 wherein said alkenes are selected from the group consisting of pentenes, methyl-1-butenes, methyl-2-butenes, hexenes, dimethylbutenes, methylpentenes, heptenes, and combinations thereof.

21. A process according to claim 3 wherein said alkadienes are selected from the group consisting of butadienes, pentadienes, hexadienes, dimethylbutadienes, methylpentadienes, heptadienes, methylhexadienes, octadienes, nonadienes, methyloctadienes, and combinations thereof.

22. A process according to claim 21 wherein said alkadienes are selected from the group consisting of pentadienes, hexadienes, dimethylbutadienes, heptadienes, and combinations thereof.

23. A process according to claim 1 wherein said 3-alkyl-substituted-2-oxazolidinone is selected from the group consisting of 3-methyl-2-oxazolidinone, 3-ethyl-2-oxazolidinone, 3-propyl-2-oxazolidinone, 3-butyl-2-oxazolidinone, and combinations thereof.

24. A process according to claim 23 wherein said 3-alkyl-substituted-2-oxazolidinone is selected from the group consisting of 3-methyl-2-oxazolidinone, 3-ethyl-2-oxazolidinone, and combinations thereof.

25. A process according to claim 24 wherein said 3-alkyl-substituted-2-oxazolidinone is 3-methyl-2-oxazolidinone.

26. A process according to claim 1 wherein the weight ratio of said solvent to said hydrocarbon-containing fluid is in the range of from about 1:1 to about 40:1.

27. A process according to claim 1 wherein the weight ratio of said solvent to said hydrocarbon-containing fluid is in the range of from about 2:1 to about 25:1.

28. A process according to claim 1 wherein said extractive distillation comprises: a reflux ratio in the range of from about 0.1:1 to about 100:1; a hydrocarbon-containing fluid entry location in the range of from about 2 percent of the total height of the packed or trayed column to about 70 percent; a solvent entry location in the range of from about 50 percent of the total height of the packed or trayed column to about 99 percent; a temperature in the reboiler vessel in the range of from about 200° F. to about 500° F.; and a pressure in the range of from about 5 pounds per square inch gauge (psig) to about 100 psig.

29. A process according to claim 1 wherein said extractive distillation process produces (i) an overhead distillate product which comprises a smaller volume percentage of said first hydrocarbon and a larger volume percentage of said close-boiling second hydrocarbon than said hydrocarbon-containing fluid, and (ii) a bottoms product which comprises said solvent and a larger volume percentage of said first hydrocarbon and a smaller volume percentage of said close-boiling second hydrocarbon than said hydrocarbon-containing fluid.

30. A process according to claim 29 wherein said extractive distillation process further comprises separating said first hydrocarbon from said solvent in said bottoms product.

31. A process according to claim 1 wherein said first hydrocarbon is selected from the group consisting of benzene, toluene, meta-xylene, ortho-xylene, para-xylene, and combinations thereof, and further wherein said close-boiling second hydrocarbon is selected from the group consisting of pentane, 2-methylbutane, hexane, 2,2-dimethylbutane, heptane, 2,2,3-trimethylbutane, 2,2-dimethylpentane, 2,4-dimethylpentane, and combinations thereof.

32. A process according to claim 1 wherein said first hydrocarbon is selected from the group consisting of cyclopentane, cyclohexane, cycloheptane, 1,2-dimethylcyclopentane, 2,3-dimethylcyclopentane, and combinations thereof, and further wherein said close-boiling second hydrocarbon is selected from the group consisting of pentane, 2-methylbutane, hexane, 2,2-dimethylbutane, heptane, 2,2,3-trimethylbutane, 2,2-dimethylpentane, 2,4-dimethylpentane, and combinations thereof.

33. A process according to claim 1 wherein said first hydrocarbon is selected from the group consisting of benzene, toluene, and combinations thereof, and further wherein said close-boiling second hydrocarbon is selected from the group consisting of pentane, 2-methylbutane, hexane, 2,2-dimethylbutane, heptane, 2,2,3-trimethylbutane, 2,2-dimetbylpentane, 2,4-dimethylpentane, and combinations thereof.

34. A process according to claim 1 wherein said first hydrocarbon is selected from the group consisting of cyclopentane, cyclohexane, and combinations thereof, and further wherein said close-boiling second hydrocarbon is selected from the group consisting of pentane, 2-methylbutane, hexane, 2,2-dimethylbutane, heptane, 2,2,3-trimethylbutane, 2,2-dimethylpentane, 2,4-dimethylpentane, and combinations thereof.

35. A process according to claim 1 wherein said first hydrocarbon is benzene or toluene, and further wherein said close-boiling second hydrocarbon is selected from the group consisting of pentane, 2-methylbutane, hexane, 2,2-dimethylbutane, heptane, 2,2,3-trimethylbutane, 2,2-dimethylpentane, and 2,4-dimethylpentane.

36. A process according to claim 1 wherein said first hydrocarbon is cyclopentane or cyclohexane, and further wherein said close-boiling second hydrocarbon is selected from the group consisting of pentane, 2-methylbutane, hexane, 2,2-dimethylbutane, heptane, 2,2,3-trimethylbutane, 2,2-dimethylpentane, and 2,4-dimethylpentane.

\* \* \* \* \*